United States Patent [19]

Gordon

[11] Patent Number: 4,619,828

[45] Date of Patent: * Oct. 28, 1986

[54] POLYSACCHARIDE EXOTOXOID CONJUGATE VACCINES

[75] Inventor: Lance K. Gordon, Newmarket, Canada

[73] Assignee: Connaught Laboratories, Inc., Swiftwater, Pa.

[*] Notice: The portion of the term of this patent subsequent to Jan. 29, 2002 has been disclaimed.

[21] Appl. No.: 568,453

[22] Filed: Jan. 5, 1984

Related U.S. Application Data

[63] Continuation-in-part of Ser. No. 395,743, Jul. 6, 1982, Pat. No. 4,496,538.

[51] Int. Cl.$^4$ .................. A61K 39/108; A61K 39/09; A61K 39/385; A61K 39/102; C07K 15/00
[52] U.S. Cl. ........................................ 424/92; 424/88; 536/1.1
[58] Field of Search ............... 424/88, 92; 260/112 R; 536/1.1

[56] References Cited

U.S. PATENT DOCUMENTS 4,356,170 10/1982 Jennings et al. ..................... 424/92

OTHER PUBLICATIONS

Schneerson, R., et al., J. Exp. Med., vol. 152, pp. 361–376, 1980.

Primary Examiner—Blondel Hazel

[57] ABSTRACT

A water-soluble covalent polysaccharide-antigen conjugate having a molecular size between 140,000 and 4,500,000 dalton and a nominal polysaccharide/protein ratio between 0.25 and 2, capable of producing T-cell dependent antibody response to polysaccharide from a number of pathogenic bacterial organisms is prepared by mixing T-cell dependent antigen with an electrophilically activated polysaccharide hapten which polysaccharide had previously been heat sized until more than 60% attained a molecular size between 200,000 and 2,000,000 dalton.

13 Claims, 3 Drawing Figures

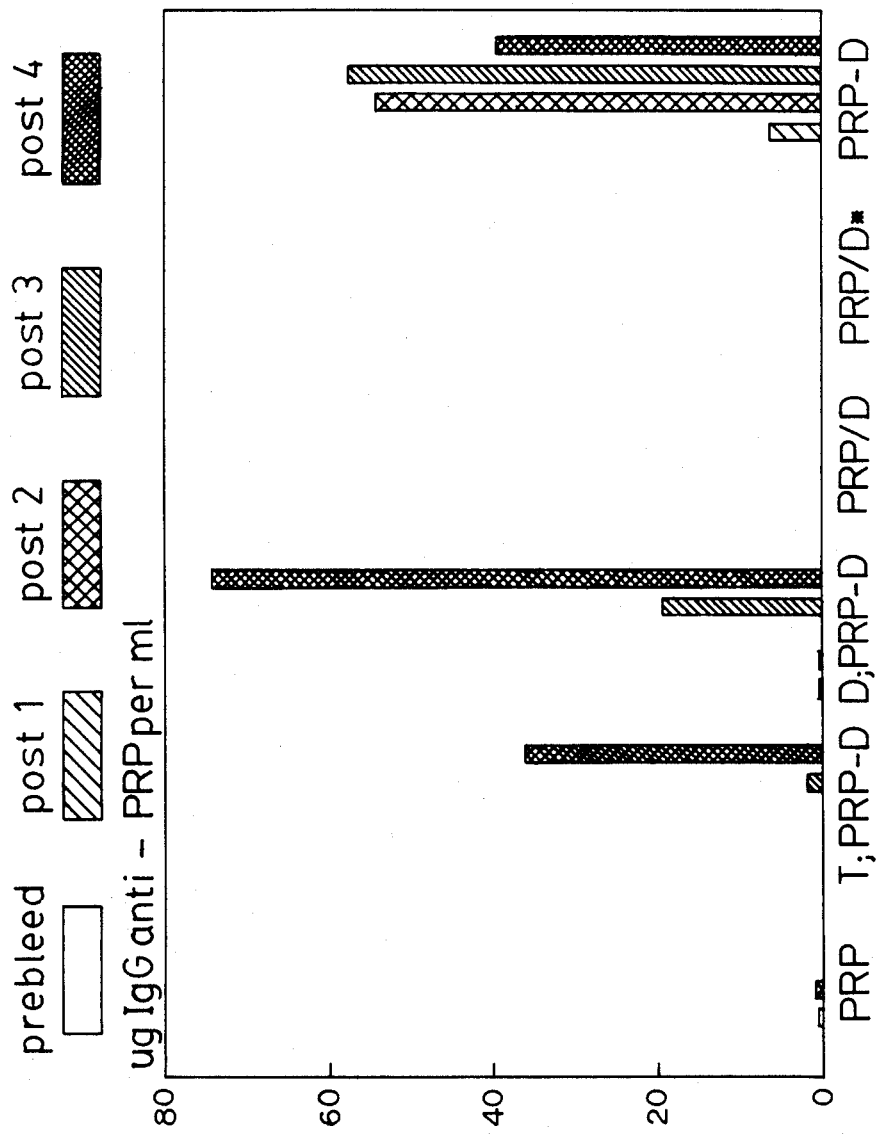

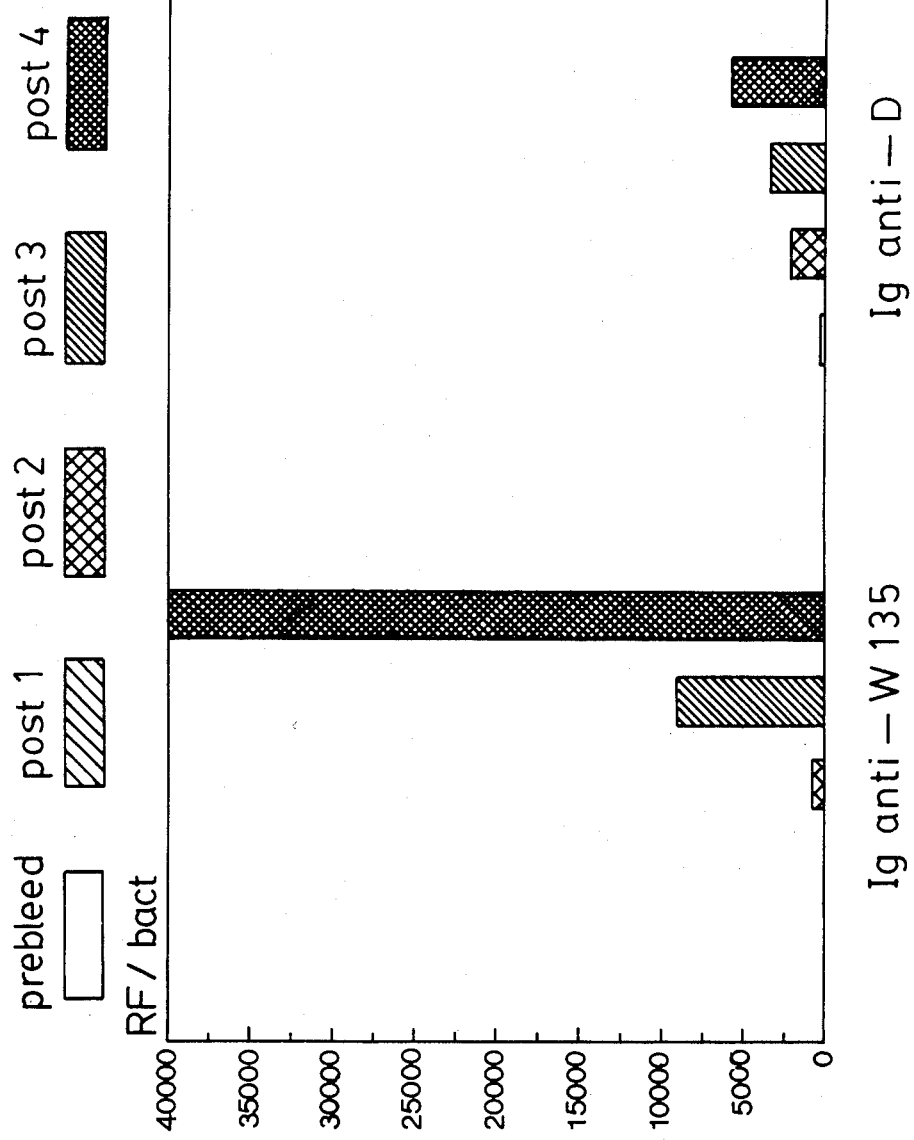

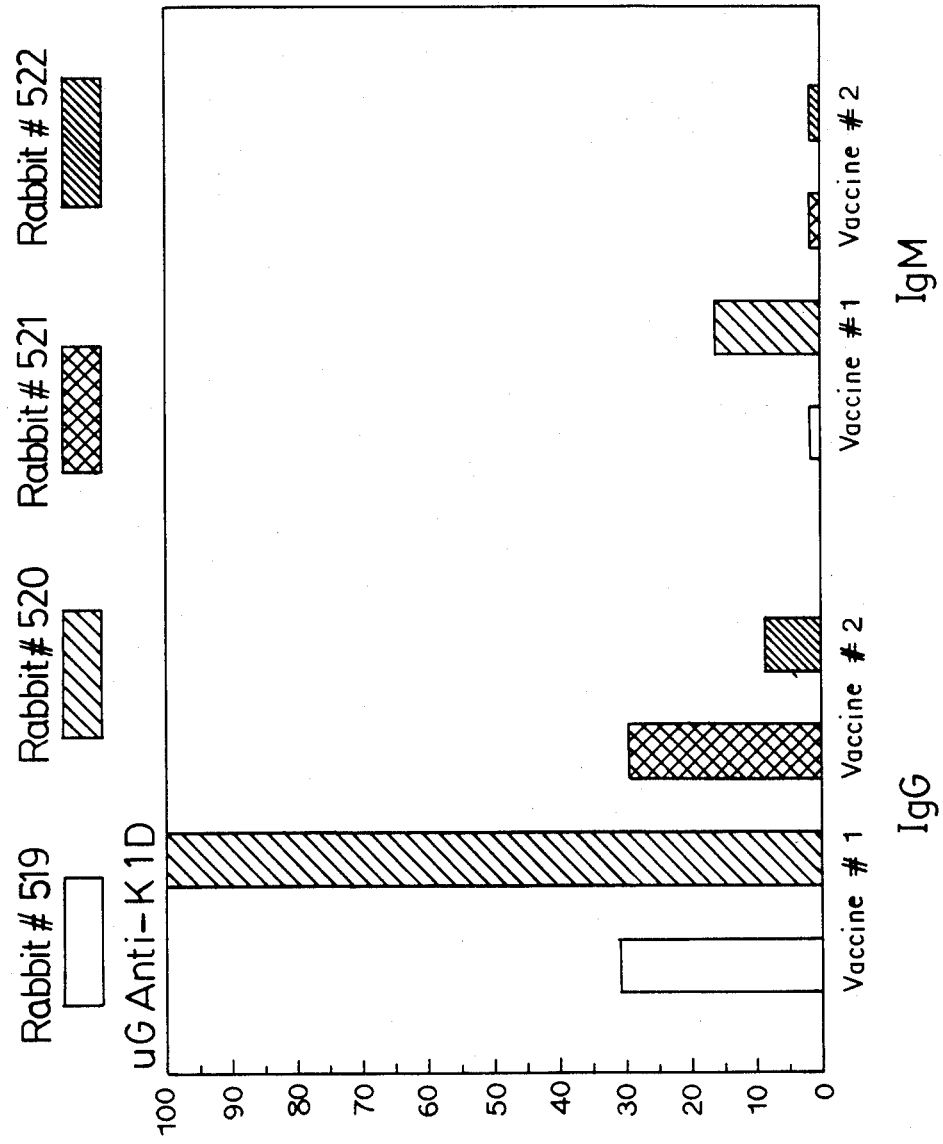

POLYSACCHARIDE EXOTOXOID CONJUGATE VACCINES

This is a continuation-in-part of Ser. No. 395,743 filed July 6, 1982, which issued as U.S. Pat. No. 4,496,538 on Jan. 29, 1985.

SUMMARY OF INVENTION

The invention relates to new polysaccharide exotoxoid vaccines, exemplified by conjugates between T-cell dependent antigens and especially diphtheria and tetanus toxoids and polysaccharide molecules from pathogenic bacterial organisms such as *Haemophilus influenzae* b, *pneumococcus, streptococcus, meningococcus,* and *Escherichia coli* and the polysaccharide haptens used for making the conjugates and the process for producing them. The invention provides pure polysaccharides (PS) from such pathogenic organisms which are adjusted by heat treatment to a molecular size principally between 200,000 and 2,000,000 Daltons. Molecular sizes stated in this application are referenced to dextran standards by gel permeation chromatography. These polysaccharides are then activated by an activator reagent, typically cyanogen bromide. The activated polysaccharide is intimately mixed with an exotoxoid, preferably diphtheria toxoid, to effect conjugation. Preferably the exotoxoid is derivatized using as a spacer a bridge of 4 to 8 carbon atoms, e.g. preparation of the adipic acid hydrazide derivative of the toxoid, either diphtheria or tetanus (D-AH or T-AH). Multiple AH units are attached to the exotoxoid molecules.

By use of this method there is obtained a antigen-polysaccharide conjugate, which can be used as a vaccine to elicit T-cell dependent responses to polysaccharides from the aforementioned organisms. The invention also makes available a conjugate vaccine useful for immunization against diseases such as diphtheria and tetanus. The potency in humans of such conjugates is greater than that of the conventional diphtheria and tetanus toxoid preparations. The methods, by careful control and removal of excess activator, provides a polysaccharide conjugate constructed of multiple molecules of antigen (exotoxoid) attached to single molecules of polysaccharide, linked through a spacer, and substantially free from cross-linked or polymeric derivatives. The formula may be generally represented as PS-Xn wherein X is the toxoid moiety and n is an integer smaller than 20, a typical average being 7-8. (The diphtheria toxoid conjugate is referred to herein as PS-D, the tetanus conjugate as PS-T without use of the integer n).

DISCLOSURE OF THE INVENTION

The development of stable humoral immunity requires the recognition of foreign material by at least two separate sets of lymphocytes. These sets are the T-lymphocytes, which modulate the function of B-cells. While some antigens, including several polysaccharides, are capable of directly stimulating B-cells to produce antibodies (T-independent antigens), most antigens (T-dependent) must be presented to the B-cells by T-lymphocytes. In the case of the vaccines of this invention, the exotoxoid portion of the vaccine is recognized by the T-cell system. Since the protein carries both its own antigenic determinants and the covalently bound PS hapten, both sets of determinants are presented by T-cells to B-cells. The result of administration of this carrier-hapten conjugate preparation is that PS is presented as a T-dependent immunogen. A T-dependent presentation of PS induces protective immunity in infants, the target population at greatest risk of many of the diseases caused by the organisms named as examples. Many of the pure polysaccharides do not induce a protective response in infants when administered alone. The conjugate vaccines of this invention are therefore of special value in small infants. In addition, the conjugates can be significantly more immunogenic in adults than the pure polysaccharides. Administration of such conjugates to women induces a high proportion of IgG antibody to the vaccine antigens, which penetrates the placental barrier during pregnancy, and thus affords protection to the infant from birth.

T-independent antigens induce B-cells to terminally differentiate into antibody secreting cells (plasma cells), while T-dependent responses are considerably more complex. After receiving a T-dependent stimulus, the B-cell population enters not only antibody production, but also proliferation and maturation. There results an increase in the number of B-cells making antibodies to PS and an increase in the number of B-cells capable of responding to a second exposure to PS. Repeated immunization results in further increases in the number of PS specific B-cells and, consequently, higher antibody titers, a booster response. In summary, T-dependent responses result in an increase in the total number of antigen responsive cells.

The PS-exotoxoid vaccines of this invention have been shown to function as T-dependent immunogens in laboratory animals. All animals in a group of rabbits serially immunized with standard doses of PS-D showed booster responses. In addition, primary immunizations with the carrier proteins used in the conjugate, e.g. diphtheria toxoid for PS-D, were shown to augment the initial response to the PS component of the PS-exotoxoid conjugate, this property should augment the response to the conjugates in children having previously received routine pediatric immunization with diphtheria and tetanus toxoids. A similar augmentation of the PS response was not seen in animals primed with an exotoxoid other than that used in the conjugate.

The vaccine of this invention is a PS-exotoxoid hapten-carrier conjugate. In such vaccines, the antigenic but weakly immunogenic hapten molecule (PS) contributes a new antigenic specificity to highly immunogenic carrier molecules such as diphtheria (D) or tetanus toxoid (T).

In a preferred embodiment of the invention, the purified diphtheria toxoid (D) used as carrier in the preparation is a commercial exotoxoid modified (derivatized) by the attachment of a 4–8 carbon spacer molecule, such as adipic acid dihydrazide (ADH), using the water-soluble carbodiimide condensation method. The modified exotoxoid, typically the adipic hydrazide derivative X-AH, is then freed from unreacted ADH. This is a soluble product, substantially free of cross-linking which is verified by lack of a substantial increase in molecular size as determined by gel chromatography and polyacrylamide gel electrophoresis.

In defining the 4–8 carbon spacer or chain linker and the method of bonding to the carrier and polysaccharide, it will be recognized by those skilled in the art that a linker of the formula X-B-X can be employed. In that formula B is an alkylene chain wherein, optionally, a heteroatom replaces one of the —$CH_2$— linkages. Thus, if the heteroatom is oxygen, the linker would be of the formula X-alkylene-O-alkylene-X. X represents a reactive nucleophilic group capable of coupling with the electrophilically activated polysaccharide and reactive to a T-cell dependent antigen, such as a hydrazido or amino group; typical examples are alkylenedicarboxylic acid, dihydrazides and alkylenediamines such as 1,6-diaminohexane.

The capsular polysaccharides of the aforementioned organisms are prepared from commercial sources such as those for licensed polysaccharide vaccines and are obtainable from Connaught Laboratories. However, while the polysaccharides are conventionally purified as a calcium salt, the use of calcium ions is avoided because they interfere with the use of carbonate buffer in the conjugation procedure. Interference by $CaCO_3$ formation can be minimized by using very low ionic strength carbonate buffer (0.005M) in the solution of the electrophilic activator (e.g. CNBr) and removing the excess cations before combination of the activated polysaccharide with the derivatized exotoxoid. Such reduction in the concentration of calcium can be achieved by the steps described in Example II describing activation of PS, in steps G through H. The molecular size of the polysaccharide is then adjusted by heating until the desired dimension for the hapten is obtained. Typically, heating of a polysaccharide solution for 15 minutes at 100° C. suffices to assure that less than 20% of the molecules are of a molecular size smaller than 200,000 dalton and less than 20% of a molecular size greater than 2,000,000 daltons. This sizing operation is important to obtain a proper conjugate.

The sized polysaccharides thus obtained are activated with an activator reagent such as a cyanogen halide or alkali metal borohydride to create an electrophilic group on the polysaccharide. A typical activator used is cyanogen bromide. Unreacted activator is exhaustively removed because, if there is a substantial residue, it causes cross-linking of the protein in the following reaction mixture. The resulting cross-linked product would trap polysaccharide, producing a lower yield of product and a higher molecular size complex differing in chemical properties and solubility from the conjugate produced herein and a vaccine which lacks the desirable properties of the vaccine of this invention.

In creating an electrophilic grouping on the polysaccharide, it will be understood that in addition to cyanogen halides or alkali metal borohydrides such as sodium borohydride, any reagent creating the same functionality is equally applicable. It will be understood that the purpose of both the active groups on the carbon chain linker and the polysaccharide is to provide means for obtaining the linkage of the polysaccharide to the carrier with a spacer between the molecules. Any reagents used to achieve this purpose fall within the scope of the invention.

The activated PS and X-AH are then combined and allowed to react in the cold. Some of the reactive groups X on the derivatized exotoxoid react with the activated sites on PS to form covalent bonds. The product is PS covalently bound to derivatized exotoxoid through a spacer bridge of formula B defined above. This reaction product is purified by gel permeation chromatography to remove any unreacted protein and low molecular size contaminants. The typical molecular size of the principal fraction is about 675,000 daltons relative to a dextran standard. A typical range for relative molecular size is 140,000 daltons to 4,500,000 daltons. The carbohydrate/protein ratio is 0.25 to 2.0.

A preservative such as thimerosal is added, in the case of thimerosal to a final concentration of 1:10,000. The bulk concentrate is filtered through a 0.2 micron membrane filter and stored in the cold.

The PS-exotoxoid conjugation product is heat resistant and water soluble. The lack of cross-linking is verified by lack of a substantial increase in molecular size from that of the starting polysaccharide as determined by gel permeation chromatography and by polyacrylamide gel electrophoresis. Heat stability assures a long shelf-life and a stable product even in unfavorable climates.

The reaction can be represented schematically in the case of CNBr as two steps:

$$PS + CNBr \rightarrow PS^* \quad (1)$$

$$PS^* + nX \rightarrow PS(-X)n \quad (2)$$

If the removal of the CNBr activator is not efficiently carried out, there occur, besides conjugation of the activated PS and exotoxoid to form PS (—X)n, such undesirable reactions of formation of X—X or multiply linked derivatives, e.g.,

$$PS^* + CNBr + nX \longrightarrow XX-PS-X + X-X-PS +$$

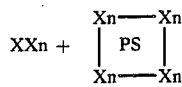
$$XX_n + \begin{array}{c} X_n \text{——} X_n \\ | \quad PS \quad | \\ X_n \text{——} X_n \end{array}$$

A typical human dose of PS-exotoxoid conjugate vaccine for subcutaneous or intradermal injection consists of 0.5 ml containing 10 micrograms of sugar or the approximate equivalent of 40 micrograms of the conjugate product. Ampoule solutions are prepared by dilution of the bulk concentrate with phosphate buffered saline solution using thimerosal as a preservative.

The product induces antibody formation in humans to both the PS and exotoxoid component.

The following examples are provided for purposes of illustrating the invention in further detail. They are not to be construed as limiting the invention in spirit or in scope.

EXAMPLE I

Preparation of PS

A. Organism

1. Capsular polyribosyl ribitol phosphate of *Haemophilus influenzae* b (PRP) was prepared from the Eagan strain. The culture was repeatedly transferred and a lyophilized seed prepared. From this lyophilized seed one additional transfer was made to prepare wet working seeds (stored at −60° C.). Fermenter lots of bacterial cells were prepared from the wet working seed.

Culture purity is determined by the following criteria:

(a) negative Gram stain characteristics;

(b) growth on agar containing NAD (diphosphopyridine nucleotide) and Hemin (Bovine Type I crystalline salt of ferriheme);

(c) failure to grow on agar without NAD or Hemin; and (d) agglutination by specific antisera (type b *Haemophilus influenzae* b, Hyland Laboratories).

2. Meningococcal strains are those used for production of the four valent meningococcal vaccine, Menomune[R]. This vaccine is compounded from the purified capsular polysaccharides of *N.meningitidis* groups A, C, Y and W135. The vaccine is licensed for human use and is available from Connaught Laboratories Inc., Swiftwater, Pa. Purity and identity of the strains are monitored by similar serologic and microbiologic procedures to those used for *H.influenzae* b above. Typing antisera were either purchased from Hyland Laboratories, or developed at Connaught. These procedures are fully documented in the product licence.

B. Cultivation and Media

1. For subculturing the bacterium, i.e., preceding inoculation of a fermenter, BHI Agar (per liter: 37 gm BHI Difco, 15 gm Bacto Agar Difco, 0.6 ml 1% NAD Sigma-Grade III and 6 ml of 0.2% Hemin (Sigma-Bovine Type 1) was employed. Cells (20 Hours) washed from an agar surface are used to inoculate *Haemophilus influenzae* b (Hib) liquid media (1 liter aliquots); these cultures are incubated with shaking until the bacterium reaches the log phase of its growth cycle. At this time, 2 liters of culture are used to inoculate each 40 liters of liquid Hib media in a fermenter and 300 ml 8% UCON (Union Carbide lubricant) is added. After 16 to 18 hours, the fermenter culture is ready for harvest.

The composition of the Hib liquid media per 100 ml is:

| | |
|---|---|
| Yeast Extract Cialysate, Difco | 5.0 gm |
| Casamino Acids, Difco | 22.5 gm |
| Sodium Phosphate, dibasic | 14.4 gm |
| Dextrose | 5.59 gm |
| Hemin | 20 gm |
| Ammonium Hydroxide (30%) | 0.1534 ml |
| NAD 1% | 0.6 ml |

When harvesting a fermenter, culture purity is determined by appropriate Gram staining and culturing techniques (see A 1-4 above). Cetavlon (hexadecyltrimethylammonium bromide) is added to the culture to a final concentration of 0.1%. After 30 minutes, at which time the bacteria have been inactivated, the solid paste is collected by centrifugation. The wet paste is stored at −70° C. until further processing.

C. Purified Polysaccharide

The extraction and subsequent purification of the PS is carried out using the following procedure:

1. Dissociation from Detergent

For each gram wet weight of paste, 10 ml of 0.4M NaCl is added. The suspension is mixed in a commercial blender for 30 seconds. The mixture is centrifuged for 15 minutes at 17,000 xG in the cold (4° C.). The supernatant is collected and ethanol is added to a concentration of 25%. This material is then centrifuged for 2 hours at 17,000 xG (4° C.) and the supernatant saved. Ethanol, at four times the volume of the supernatant, is added and the material held overnight at 4° C.

2. Removal of Nucleic Acids

The material is centrifuged for 5 minutes at 2800 xG (4° C.). The sediment is collected and resuspended in Tris-MgSO$_4$ buffer at one-fourth the volume originally used to extract the paste. The composition of the Tris buffer is as follows per liter of distilled water:

| | |
|---|---|
| tris-hydroxymethylamino-methane (Sigma) | 6 gm |
| MgSO$_4$.7H$_2$O | 246 mg |

-continued

| | |
|---|---|
| thimerosal (Elanco) | 50 mg |

The pH is adjusted to 7.0±0.2 with concentrated hydrochloric acid.

Deoxyribonuclease I 1.5 mg (Sigma D-0876) and ribonuclease-A 0.75 mg (Sigma-Type 1-AS, R-5503) per 100 gm of original wet paste are added. The material is placed in a dialysis bag and incubated for 18 hours at 37° C. versus 18 liters of Tris-MgSO$_4$ buffer.

3. Removal of Proteins

The material is further processed to remove protein components by adding an equal volume of phenol-acetate solution (135 ml of 10 percent (w/v) sodium acetate combined with 454 gms of phenol). The material is then shaken for 30 minutes (4° C.), centrifuged for 15 minutes at 17,000 xG and the aqueous phase collected. Two additional phenol extractions are conducted followed by dialysis of the last aqueous phase against distilled water.

The material at this stage constitutes the bulk liquid capsular polysaccharide (PS) and is stored at −20° C. until further processing (Section D below).

4. Assessment of Quality of Polysaccharide

The quality of the bulk PS is judged based on the analysis of a liquid sample that is removed. Ethanol is added (4 volumes), then CaCl$_2$ (final concentration of 0.02M) and the PS is precipitated. The PS is sedimented by centrifugation and dried under vacuum over a dessicant. A thermogravimetric analysis (TGA) is used to determine the moisture content. Further analyses are calculated on a dry weight basis.

Criteria for acceptance include:

(a) For the case of *H.influenza* b analysis of sugar: greater than 30 percent, similar criteria to ensure a minimal porportion of the polysaccharide are used for other organisms.

(b) analysis of protein (Lowry method): less than 1 percent, (c) analysis of nucleic acids (U.V. adsorbance): less than 1 percent, and (d) precipitation with specific immune sera (counterimmunoelectrophoresis method).

In addition, the molecular size is determined by suitable gel permeation chromatography. The polysaccharide is monitored for endotoxin by Limulus Lysate testing and by rabbit pyrogenicity testing.

A typical lot has the following characteristics:

(a) Protein content, 0.5%

(b) Nucleic acid content, 0.35%

(c) Residual bovine antigens: No contamination of the purified PS by bovine RNA-ase and the DNA-ase used in preparation of the polysaccharide, as measured by radioimmunoassay.

(d) Endotoxin content was measured by the Limulus Amoebocyte to Lysate Assay (LAL): 200 ng/mg PRP.

(e) Kd on CL-4B Sepharose: 0.30. A value of 0.30 corresponds to an approximate molecular weight of 1,125,000 daltons relative to dextran standards.

D. Preparation of Polysaccharide (PS) Reagent

The polysaccharide is thus purified as a solution but calcium is not avoided in the purification procedure. (Conventional polysaccharide purification yields a calcium salt, but calcium can combine with the carbonate buffer used herein below during conjugation to form a precipitate.)

The size of the polysaccharide is adjusted by controlled heating typically at 100° C. for a time proportional to the degree of size change needed. Size of the polysaccharide is adjusted so that less than 20% elutes from a CL-4B Sepharose column in the void volume, and less than 20% elutes with a Kd greater than 0.5. The principal fraction has a molecular size of 200,000 to 2,000,000 daltons.

EXAMPLE II

Activation of PS

A. The polysaccharide is cooled in an ice bath to 4° C. in a reaction vessel equipped with a magnetic stirrer. The initial volume of PS at the concentration of 25 mg/ml (20-30 mg/ml range) in distilled water is recorded. Then sodium chloride is added to a concentration of 0.85%.

B. The pH of the resulting solution of the sodium salt of the polysaccharide is raised to 10.5-11.0 by addition of 1N sodium hydroxide. (This range is chosen because at a lower pH there is less reaction with cyanogen bromide and at higher pH the polysaccharide breaks down.)

C. Dry cyanogen bromide is dissolved in 0.005N sodium bicarbonate buffer of pH 10.5-11.0 and immediately (within 10 minutes of preparation) is added to the reaction vessel in a proportion of 0.4 mg/mg PS.

D. The pH of the mixture is adjusted to and maintained at 10.5-11.0 for 6 minutes by addition of sodium hydroxide.

E. The pH is then dropped to 6.0 with 1N NCl. (Acid pH stabilizes the activated sites created on the polysaccharide by cyanogen bromide. Lowering the pH further results in hydrolysis of the PS.)

G. There is added an equal volume of saline, pH 6.0, pre-chilled to 4° C.

H. The cyanogen bromide-polysaccharide mixture is transferred to a concentrator apparatus and concentrated to the initial volume recorded at Step A.

I. Steps G and H are repeated a total of 10 times. Thus about 99.9% of the unconsumed cyanogen bromide is removed while the polysaccharide concentration is maintained at 25 mg/ml. If the cyanogen bromide is not removed, it reacts with the diphtheria exotoxoid used below. These steps also serve to reduce the calcium concentration and the formation of calcium carbonate at later steps in the method.

EXAMPLE III

Preparation of a D-AH Carrier

A. Commercial diphtheria exotoxoid (D) in distilled water is concentrated to 20-40 mg/ml, typically 35 mg/ml over a membrane that retains molecules greater than 10,000 daltons in a positive pressure stirred concentrator.

B. A dry mixture of 8 mg adipic acid dihydrazide (ADH) per my protein and 0.75 mg 1-ethyl-3-(3-dimethylaminopropyl) carbodiimide (EDAC) per mg protein are placed in a reaction vessel equipped with an efficient stirrer and a pH probe to permit monitoring and control of pH.

C. The diphtheria exotoxoid is then added to the reaction vessel making the proportion of the reactants:

| | | |
|---|---|---|
| diptheria exotoxoid | = | 35 mg protein/ml |

-continued

| | | |
|---|---|---|
| ADH | = | 8.0 mg/mg protein |
| EDAC | = | 0.75 mg/ml protein |

(The use of acetate buffer on sequential addition of ADH and EDAC results in a persistent flocculent precipitate. The reactants have a sufficient buffering capacity of their own.)

D. The pH is immediately adjusted to 4.7 and maintained at 4.7±0.2 for a minimum of 2 hours.

1. The course of the chemical reaction can be followed on the recorder of the pH controller. If necessary, the reaction is allowed to proceed past 2 hours until the pH is stable for at least 15 minutes (i.e. 15 minutes without needing HCl addition to control pH).

2. The amount of HCl consumed is recorded as a process check.

3. Temperature change in the reaction vessel is also monitored.

E. The reaction product is dialyzed at 4° C. against two changes of saline, a minimum of 100 volumes and 8 hours per change.

F. It is then dialyzed against two changes of phosphate buffered saline, minimum volume, time and temperature as for Step E.

G. The product (D-AH) is concentrated back to 25 mg/ml protein with a positive pressure apparatus and 10,000 dalton membrane. (Ultrafiltration, dialysis and concentration can be substituted for steps E, F and G.)

H. The concentrate is sterile filtered (0.2 u filter) and stored at 4° C. Assay of a sample of a typical lot of such D-AH carrier showed a ratio of 38.3 microgram ADH/mg DT. Chromatography of that sample showed a Kd value on CL-48 Sepharose of 0.75 which corresponds to an approximate molecular weight of 139,000 daltons relative to protein standards.

EXAMPLE IV

Formation of the Covalent Polysaccharide-diphtheria Toxoid Conjugate (PS)

A. The diphtheria toxoid adipic acid hydrazide carrier (D-AH) of Example III, at a concentration of 25 mg/ml, is treated with sodium bicarbonate to a concentration of 0.5M and the pH is adjusted to 8.5. (Significantly lower salt concentrations result in the formation of a gel in the final reaction mixture with activated polysaccharide.)

B. In a reaction vessel which can be sealed, an equal amount of the washed PS solution produced in Example II is added and the pH should be stable at 8.4–8.6. (If CNBr has not been removed, the pH will drift rapidly downward and a copious precipitate will form. This reaction occurs even in the absence of polysaccharide. There should not be a significant change of the physical appearance of the reactants on combination.)

C. The reaction mixture is tumbled for 15–18 hours at 4° C.

D. The conjugate is purified by gel permeation chromatography on Sephacryl-300 equilibrated in phosphate buffered saline to remove unreacted protein and material of molecular size less than 140,000 daltons in size. (If the starting polysaccharide is too small it will not be possible to separate the conjugate from unreacted protein in this manner.)

E. Samples of this purified conjugate are removed for chemical analysis, described in the following section of this example.

F. Thimerosal is added to the purified conjugate to a concentration of 1:10,000 and the product is stored at 4° C. until analysis.

G. The product is 0.2 micron sterile filtered. (If the polysaccharide is not sized as described in Example I (D), i.e., if it is oversize, the resulting conjugate will not be filterable.)

Analysis

Tests performed on the bulk concentrate of Example IV using *Haemophilus influenzae* b as an example gave the following results:

(a) Ribose content: 156.5 microgram/ml. (For the calculation of PRP values in Example V, a conversion factor of 2 is used to calculate a nominal polysaccharide concentration based on the empirically determined ribose concentration.)

(b) Protein content: 330 microgram/ml (c) Ribose/protein ratio: 0.47 (limits 0.25-1.0)

(d) Chromatographic analysis on Sepharose CL-2B gave the chromatographic profile which shows a homogeneous distribution of conjugate molecules as a single peak.

(e) Kd (polysaccharide): 0.36 using Sepharose CL-4B, 0.77 using CL-2B. Determined by individual fraction ribose assay for PS. A value of 0.36 on CL-4B corresponds to an approximate molecular size of 674,000 daltons relative to dextran standards.

(f) KD (protein): 0.36 using Cl-4B; 0.71 using Cl-2B. Determined by individual fraction Lowry assay for protein. The change in the Kd value of the diphtheria exotoxoid from 0.75 to 0.34 on Cl-4B shows that the conjugation of protein with polysaccharide forms a molecule which is chromatographically different from either raw material.

(g) Free Protein: Less than 5%. Free protein represents derivatized diphtheria carrier protein which has not been bound to PRP. It is determined by comparing the amount of protein that elutes from Sepharose CL4B in the position of a diphtheria exotoxoid sample relative to the total eluted protein.

(h) Endotoxin Content: 1 ug/ml. Endotoxin was quantitated by the Limulus Amoebocyte to Lysate Assay (LAL). The endotoxin content amounts to 64 ng per 10 ug ribose human dose of PS-D.

(i) Pyrogenicity: The bulk concentrate meets the U.S. standard for nonpyrogenicity using a weight equivalent (human) dose of 0.15 ug ribose per milliliter per kilogram body weight of rabbit.

(j) Polyacrylamide Gel Electrophoresis (PAGE): PAGE analysis was performed to obtain supporting evidence of purity and covalent bonding between polysaccharide and protein. While free carrier (D) bands just over halfway into the rod gel, at approximately the position of catalase (60,000 MW), the PS-D conjugate was not able to enter the gel (prior to the position of thyroglobulin, 330,000 MW). PS-D showed a single band at the origin.

(k) Cyanogen Bromide: While cyanogen bromide (CNBr) is used in the first steps before preparing a PS-D conjugate, it is subsequently excluded from the product. Several steps of the process contribute to the reduction of CNBr content. However, final purification of the vaccine by gel permeation chromatography removes any contaminants below 100,000 MW. This purification precludes contamination with residual traces of free CNBr or its degradation products. Chemical testing showed less than 1.5 parts per million of free CNBr.

(l) Heat Stability: A study for the heat stability of PS-D conjugate vaccine was performed. The bulk material was concentrated 40 fold and three 3 ml samples were taken. The first was kept in a 4° C. water bath for 16 hours, and the third was heated in a 100° water bath for 30 minutes. The tests performed were for protein and ribose content, gel permeation chromatography with sepharose Cl-4B and SDS-polysaccharide gel electrophoresis (PAGE).

The results showed no significant change in ribose or protein content between the samples compared to the results in test (a) and (b) above. The chromatographic analyses showed a minor decrease in the molecular size of the conjugate material as conditions were made increasingly harsh. However, upon fractional analysis of these samples by measuring absorbance at 254 nm, the material maintained only one peak coinciding with the polysaccharide peak and no free protein peak appeared; the results are thus comparable to those in (d) and (g) above. This demonstrates that the linking between the protein and polysaccharide did not break but the decrease in molecular size was due to the breaking of bonds within the linear polysaccharide. This was further demonstrated by comparison of PAGE analysis of these samples, to the results described under (j) above; free protein was not detectable in any of the samples even in the presence of a detergent (sodium dodecyl sulfate). This strongly affirms the covalency of the derivatized protein-polysaccharide linkage and its stability through high temperature treatment.

Similar results have been obtained by applying the same procedure to meningococcal and *E.coli* polysaccharides.

Specific samples include:

(1) A conjugate of Group B meningococcal polysaccharide ($B^{SSS}$) and derivatized diphtheria toxoid. The polysaccharide in this conjugate is determined by assaying for sialic acid (nominal conversion from sialic acid to polysaccharide concentration is 1.2). The diphtheria toxoid derivative used contained 49.5 ug ADH per mg of toxoid protein. The purified conjugate contained 222.5 ug of sialic acid and 253.8 ug of protein per mg of conjugate. The sialic acid to protein ratio was 0.88. The polysaccharide and protein coeluted from Sepharose CL4B in a position characteristic of the polysaccharide and distinct from unreacted diphtheria toxoid. The covalently linked protein could not be separated from the polysaccharide on SDS-polyacrylamide gels (SDS-PAGE).

(2) A similar conjugate was prepared with Group C meningococcal polysaccharide. This conjugate contained 867 ug of sialic acid and 204 ug of diphtheria toxoid protein per ml.

EXAMPLE V

PS-D Immunogenicity Testing

This experiment was designed to show T-cell dependency as evidenced by: carrier dependency, carrier specificity, booster effect, and change in Ig class. This experiment was carried out in two parts: (1) an initial priming sequence of two injections; (2) a challenge sequence of two injections.

Materials

1. PS-D bulk concentrate, Example 4.
2. Tetanus Toxoid (T)
3. Diphtheria Toxoid (D).
4. *H.influenzae* b capsular polysaccharide (PRP).
5. PS/D, a mixture of 20 ug PRP (10 ug ribose) and 20 ug D.
6. PS/D-AH, a mixture of 20 ug PRP (10 ug ribose) and 20 ug D-AH.

Method

All immunizations were administered subcutaneously without adjuvant in 1 ml volumes. All doses containing PRP were adjusted to 10 ug ribose per 1 ml dose. Unconjugated exotoxoid doses were adjusted to 20 ug protein per 1 ml dose. A rotating schedule was used with immunizations spaced 14 days apart. Each immunization was followed by a bleed 10 days later. All preparations were diluted in phosphate buffered saline containing 0.01% thimerosal. Aliquots were prepared as four dose vials, and stored at $-20°$ C. Three rabbits were immunized in each group.

Serology

Sera were assayed by the solid phase radioimmunoassay (SPRIA) for anti-PRP, anti-D, and anti-T as indicated. Antibody levels were quantitated as microgram IgG and IgM per ml.

Protocol

| Group | Primary | Secondary | PRP | DT | TT |
|---|---|---|---|---|---|
| 1 | PS | PS | + | | |
| 2 | T | PS-D | + | + | + |
| 3 | D | PS-D | + | + | + |
| 4 | PS/D | PS/D | + | + | |
| 5 | PS/D-AH | PS/D-AH | + | | |
| 6 | PS-D | PS-D | + | + | |

Schedule

Rabbits were pre-bled and immunized according to group every 14 days. Each immunization was followed by a post-bleed 10 days later. The first two injections were made with the primary immunogen, while the third and fourth injections were made with the secondary immunogen.

Anti-PS response is demonstrated in FIG. 1. The mean level of IgG antibody to *Haemophilus influenzae* b capsular polysaccharide in the six experimental groups of rabbits (three animals per group) are graphically illustrated. Groups are labelled on this figure in accordance with the above protocol. Prebleed levels were less than 1 ug/ml for all rabbits.

IgG responses were seen only following immunization with the PS-D conjugate vaccine. Priming the rabbits in group 3 with diphtheria toxoid accelerated the response to PS-D, while priming the tetanus toxoid (group 2) had no effect.

FIG. 2 demonstrates the immune response to a conjugate of group W135 meningococcal polysaccharide and diphtheria toxoid. The T-dependent booster response is demonstrated by the sequential rise in antibody titre after each immunization. Antibody titre in this experiment is expressed as RF (relative factor) by comparison with a standard antiserum. This experiment was also conducted in rabbits. Immunisation of rabbits with the pure polysaccharide alone does not elicit a detectable antibody response.

FIG. 3 shows the level of antibody to *E.coli* K1 polysaccharide induced by two separate conjugates of K1-D prepared by the methodology disclosed above. Both vaccines induced the predominantly IgG antibody response characteristic of a T-dependent vaccine. The purified polysaccharide alone does not induce a detectable antibody response in rabbits.

TETANUS TOXOID

EXAMPLE VI

Preparation of T-AH Carrier and Formation of Covalent Polysaccharide-Tetanus Toxoid Conjugate (PS-T)

In the procedure of Example III, a commercial tetanus toxoid is used in the place of diphtheria toxoid to produce the adipic acid hydrazide derivative.

Assay of a sample of a typical lot of T-AH carrier showed a ratio of 53.9 microgram ADH/mgT. Chromatography of that sample showed a Kd value of CL-4B Sepharose of 0.66 which corresponds to an approximate molecular weight of 227,000 relative to protein standards.

Polysaccharide conjugates with the adipic hydrazide derivate of tetanus toxoid are formed using the same procedures as for D-AH, as described in Example IV.

Analysis of a typical lot of PS-T showed 142.6 micrograms of polysaccharide and 260 micrograms of protein per ml. The conjugate was soluble and 0.2 micron filterable. When chromatographed on CL-4B the protein component demonstrated a Kd of 0.30 and the polysaccharide component a Kd of 0.37.

It will be understood to those skilled in the art, that while the body of our disclosure gives examples for *Haemophilus influenzae* b, *Meningococcus*, and *E.coli*, the method could be applied to any organism having a polysaccharide antigen in the cell wall. It will also be understood that the concept of a hapten combined through a linker to an antigen to give a conjugate having enhanced immunological response to the hapten is part of our invention.

What is claimed is:

1. A water-soluble, heat resistant conjugate of a polysaccharide, obtained from a pathogenic bacterial organism, covalently bound to a T-cell dependent antigen capable of producing a T-cell dependent antibody response to polysaccharides from the said organism of molecular size above 140,000 and below 4,500,000 daltons as referenced to dextran standard by gel permeation chromatography, and having a polysaccharide/protein ratio between 0.25 and 2, prepared by mixing a T-cell dependent antigen with a spacer compound of the formula X-B-X, wherein B is a $C^{4-8}$ alkylene in which a $—CH_2—$ linkage can optionally be replaced by an $—O—$ linkage and wherein X is a nucleophilic group capable of reacting with said antigen, mixing the resulting derivatized antigen with an electrophilically activated polysaccharide obtained from the said bacterial organism, which polysaccharide had previously been sized by heating until more than 60% of the polysaccharide was adjusted to a molecular size between 200,000 and 2,000,000 dalton as referenced to dextran standard by gel permeation chromatograpy.

2. A conjugate of claim 1 where said organism is a strain of *meningococcus*.

3. A conjugate of claim 1 where said organism is *E. coli*.

4. A conjugate of claim 2 where said organism is a strain of *pneumococcus*.

5. A conjugate of claim 1 wherein said organism is a strain of *streptococcus*.

6. A conjugate of claim 1 wherein X-B-X is a dicarboxylic acid hydrazide.

7. A conjugate of claim 6 wherein said dicarboxylic acid is adipic acid.

8. A conjugate of claim 1 wherein said T-cell dependent antigen is diphtheria toxoid.

9. A conjugate of claim 1 wherein said T-cell dependent antigen is tetanus toxoid.

10. A conjugate of claim 1 wherein said electrophilically activated polysaccharide is activated by use of a cyanogen halide as activator.

11. A conjugate of claim 10 wherein said cyanogen halide is the bromide.

12. A conjugate of claim 1 wherein said electrophilically activated polysaccharide is activated by use of an alkali metal borohydride as activator.

13. A conjugate of claim 12 wherein said alkali metal borohydride is sodium borohydride.

* * * * *